(12) United States Patent
Mott et al.

(10) Patent No.: US 8,005,280 B2
(45) Date of Patent: Aug. 23, 2011

(54) OPTICAL IMAGING CLINICAL SAMPLER

(75) Inventors: Donald R. Mott, Baldwinsville, NY (US); Wie Lee, Manlius, NY (US); Mark William Macko, Camillus, NY (US)

(73) Assignee: Jadak, LLC, North Syracuse, NY (US)

( * ) Notice: Subject to any disclaimer, the term of this patent is extended or adjusted under 35 U.S.C. 154(b) by 922 days.

(21) Appl. No.: 11/954,298

(22) Filed: Dec. 12, 2007

(65) Prior Publication Data

US 2009/0154776 A1 Jun. 18, 2009

(51) Int. Cl.
*G06K 9/00* (2006.01)
*G01N 35/00* (2006.01)

(52) U.S. Cl. .......... 382/128; 422/403; 422/68.1; 435/4; 436/161

(58) Field of Classification Search .................. 382/100, 382/128; 356/39, 40, 41; 435/4–40; 436/161, 436/162, 501, 510; 422/400, 401, 402, 403, 422/68.1, 69, 70
See application file for complete search history.

(56) References Cited

U.S. PATENT DOCUMENTS

| | | | |
|---|---|---|---|
| 5,408,535 A * | 4/1995 | Howard et al. ............... 382/128 |
| 5,648,274 A | 7/1997 | Chandler | |
| 5,671,735 A | 9/1997 | MacFarlane et al. | |
| 5,976,896 A | 11/1999 | Kumar et al. | |
| 5,985,675 A | 11/1999 | Charm et al. | |
| 6,312,961 B1 | 11/2001 | Voirin et al. | |
| 6,319,466 B1 | 11/2001 | Markovsky et al. | |
| 6,475,805 B1 | 11/2002 | Charm et al. | |
| 6,710,879 B1 | 3/2004 | Hansen et al. | |
| 6,716,393 B2 * | 4/2004 | Lappe et al. ................. 422/68.1 |
| 6,720,160 B2 | 4/2004 | Wolde-Mariam | |
| 7,070,920 B2 * | 7/2006 | Spivey et al. ...................... 435/4 |
| 7,313,257 B2 * | 12/2007 | Roman ......................... 382/128 |
| 7,444,005 B2 * | 10/2008 | Bachur et al. ................. 382/107 |
| 2003/0049849 A1 * | 3/2003 | Mori et al. ....................... 436/46 |
| 2003/0087325 A1 | 5/2003 | Khayyami | |
| 2003/0207442 A1 | 11/2003 | Markovsky et al. | |
| 2004/0096356 A1 | 5/2004 | Degelaen et al. | |
| 2005/0014281 A1 | 1/2005 | Langeveld et al. | |
| 2005/0203353 A1 * | 9/2005 | Ma et al. ....................... 600/315 |
| 2005/0249633 A1 * | 11/2005 | Blatt et al. ....................... 422/56 |
| 2005/0261270 A1 | 11/2005 | Wong et al. | |
| 2006/0014227 A1 | 1/2006 | Fleming et al. | |
| 2008/0064119 A1 * | 3/2008 | Panotopoulos ............... 436/514 |
| 2010/0291588 A1 * | 11/2010 | McDevitt et al. .............. 435/7.2 |

FOREIGN PATENT DOCUMENTS

| | | |
|---|---|---|
| EP | 0418113 A2 | 3/1990 |
| WO | WO2005/005656 | 1/2005 |
| WO | WO2005/118838 | 12/2005 |

* cited by examiner

*Primary Examiner* — Jon Chang
(74) *Attorney, Agent, or Firm* — David L. Nocilly; Bond Schoeneck & King

(57) ABSTRACT

A clinical sampling system including a reader capable of optically imaging a test cartridge presented thereto and then automatically determining the presence and concentration of a target compound in a liquid sample placed on the test cartridge. The reader includes an optical imaging unit for illuminating, imaging, and interpreting the test cartridge. The test cartridge houses a reaction strip having a control region and a sample region that reacts to a liquid sample placed on the strip. The presence and concentration of the target compound are interpreted by determining the relative reflected intensities of the control region and sample region and calculating the ratio of the reflected intensities relative to the reflected intensity of the background.

12 Claims, 17 Drawing Sheets

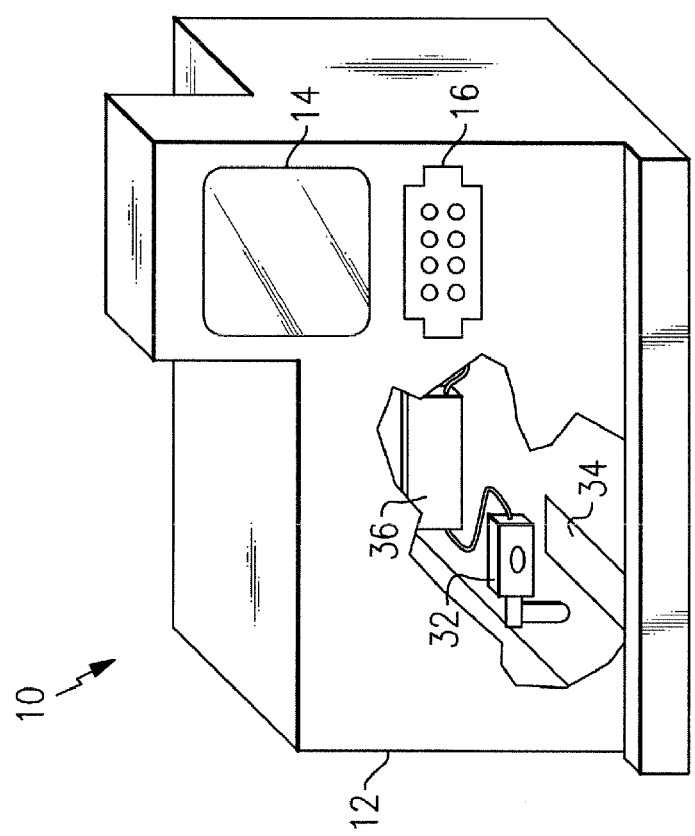

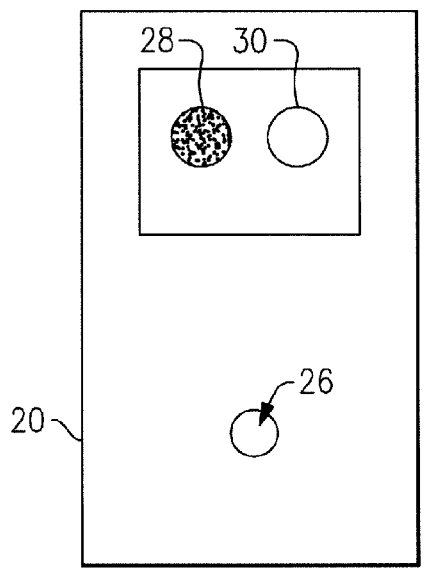
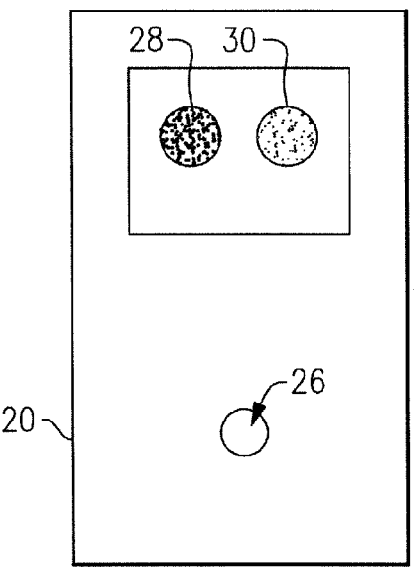
FIG.5A  FIG.5B
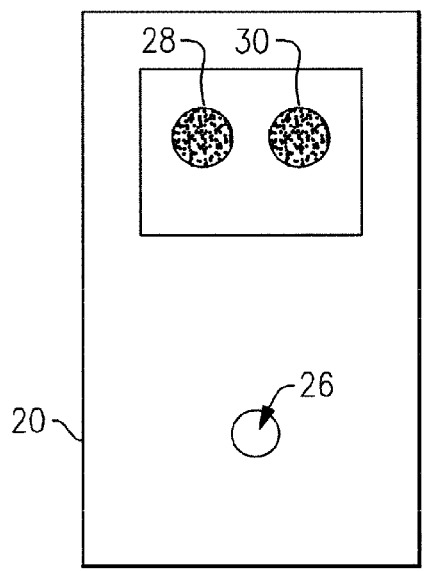
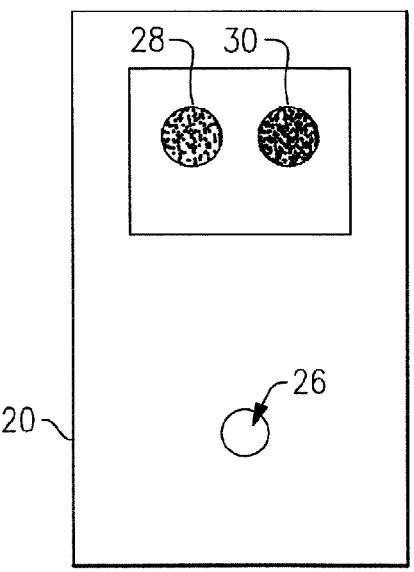
FIG.5C  FIG.5D

OPTICAL IMAGING CLINICAL SAMPLER

BACKGROUND OF THE INVENTION

1. Field of the Invention

The present invention relates to clinical samplers and, more specifically, to clinical samplers having optical imaging capabilities for automatically analyzing test materials and results.

2. Description of the Related Art

Some forms of clinical testing, such as microbial or contaminant testing of food products, involve the reaction of testing strips to a liquid sample of the product to be tested. After exposure to the product, testing strips are allowed to develop and are then examined to determine the results of any reaction to target compounds in the liquid sample. In some cases, the developed strips are inserted into a strip reader for automated testing and analysis of the test results. For example, some readers use photodiodes to simply register the presence or absence of a reaction on the strip. These systems, however, are unable to provide an indication of the concentration of the target compounds in the samples.

More sophisticated readers use photodetectors to detect fluorescence emitted from the sample liquids after reactions with marker compounds. The presence or absence of target compounds is then determined based on the wavelength and strength of the fluorescence. These systems are frequently unable to detect small changes in the test strip, which leads to inaccuracies in the test results.

Some systems for determining the presence of a substance in a sample react the sample with a microchip having fluorescing compounds embedded therein, and then use a photodetector to determine whether light is being emitted from the reacted sample and microchip. Other sample analysis systems use a testing array or plate together with a conventional optical scanner, such as that used in connection with a personal computer, to acquire a color image of sample array. The color image of the sample wells in the array is then analyzed to determine the relative concentrations of target compounds in the sample liquid based on which sample wells have reacted and which have not. These systems are very complex, however, and require sophisticated instruments or components, such as fluorescent compounds, specifically tailored microchips, and multiple reaction vessels or wells.

BRIEF SUMMARY OF THE INVENTION

It is therefore a principal object and advantage of the present invention to provide a clinical sampling system that may accurately determine the concentration of a target compound in a liquid sample.

It is another object and advantage of the present invention to provide a clinical sampling system that will reliably determine the concentration of a target compound in a liquid sample.

It is a further object and advantage of the present invention to provide a clinical sampling system that is simple to use.

In accordance with the foregoing objects and advantages, the present invention provides a clinical sampling system comprising a conventional test strip having a control or reference region and a sample region that is exposed to a sample liquid, developed, and then positioned in a reader having an optical imager that acquires an image of the sample region and the control region. The image of the test strip is then digitally processed and the results are interpreted to provide an indication of the relative amounts of target compounds, such as antibiotics, that may be present in the sample liquid.

BRIEF DESCRIPTION OF THE DRAWINGS

The present invention will be more fully understood and appreciated by reading the following Detailed Description in conjunction with the accompanying drawings, in which:

FIG. 3 is a partial cutaway view of a system according to the present invention.

FIGS. 5A-D are front views of a test cartridge according to the present invention.

DETAILED DESCRIPTION OF THE INVENTION

Figure 1:
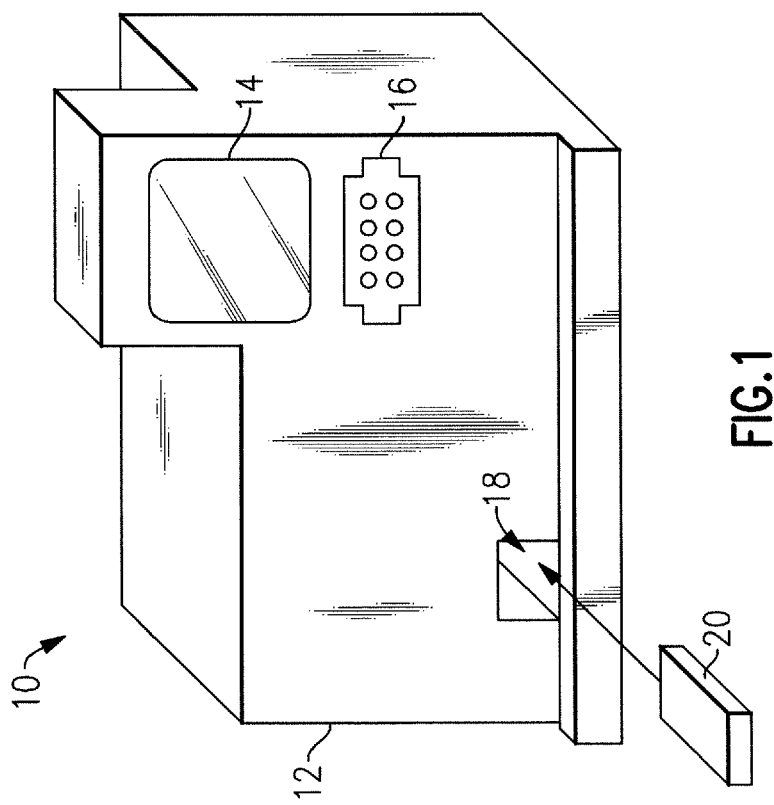
FIG. 1 is perspective view of a system according to the present invention.

Referring now to the drawings, wherein like reference numerals refer to like parts throughout, there is seen in FIG. 1 a clinical sampling system 10 according to the present invention. System 10 generally comprises a reader 12 having a display screen 14 for providing a user with information and a control pad 16 for allowing a user to input information and to control the operation of reader 12. Alternatively, display screen 14 may comprise a touch screen for user input. Reader 12 further includes a slot 18 formed therein for selective insertion, positioning, removal of a test cartridge 20.

Figure 2:
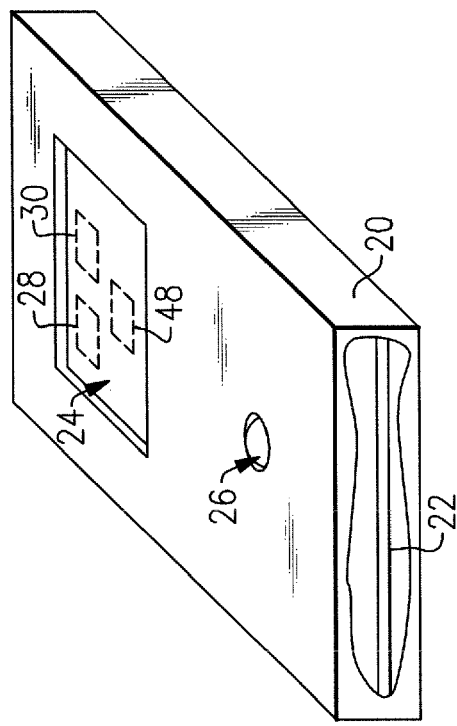
FIG. 2 is a perspective view of a test cartridge according to the present invention.

Referring to FIG. 2, test cartridge 20 houses a reaction strip 22 therein for indicating the presence of absence of a predetermined compound in a sample. Cartridge 20 includes a first opening 24 formed therein for viewing a region of strip 22. Cartridge 20 may further include a second opening 26 formed therein which exposes a second region of strip 22 for the application of a liquid sample onto strip 22.

Strip 22 preferably includes a control region 28 and a sample region 30 visible through first opening 24 in cartridge 20 that are compared to indicate the presence and concentration of one or more target compounds in a liquid sample. For example, sample region 30 of strip 22 may be pretreated with an indicating substance that reacts with a target compound to provide a visible indication of the presence of the compound, and control region 28 is provided with a fixed optical density to be used as comparison to detect relative differences in optical density with respect to control sample 30.

As seen in FIG. 2, a liquid sample may be placed onto strip 22 through second opening 26 and allowed to migrate along strip 22 until encountering sample region 30. It should be obvious to those of skill in the art that it may be necessary to allow strip 22 to develop for a given time period after placing a sample thereon, or that strip 22 may need to be incubated at a given temperature for proper development depending on the target compound and the indicating compound chosen for strip 22.

Referring to FIG. 3, reader 12 includes an imaging unit 32 positioned therein for obtaining optical images of cartridge 20 when it is inserted into reader 10 along insertion path 34. The quality of images taken by imaging unit 32 depends on the axial and lateral alignment of imaging unit 32 relative to the insertion path 34 such that optical distortion is minimized. Imaging unit 32 is optimally positioned within its focal distance, such as at a distance of 3.0 to 3.5 inches above cartridge 20, where this distance is a function of the focal length of the imaging unit and any intervening structure, such as a mirror, which may be used for alignment purposes.

Imaging unit 32 should further be programmed to obtain images of strip 22 using an exposure that will enable optimal use of the imaging unit A/D converter dynamic range without saturation. This is achieved by adaptive exposure techniques based on mean reflected intensity measures in one or more background regions 48. For example, imager 30 having an 8-bit A/D converter would use an exposure time that is adjusted to produce a mean reflected intensity of between 200 and 240 counts, measured in the background regions 48 of sample strip 22. It should be recognized that these parameters are dependent on the type of imager 30 used and different imagers 30 will require different parameters depending on the number of bits in the A/D converter and the sensitivity of the light sensing array of imager 30. In addition, the exposure count used will depend on the strength of the illumination source and the mechanism used to control exposure time. In addition to compensating for variations in substrate optical density, this adaptive technique can also provide compensation for long term deterioration of illumination source 38. The adaptive exposure technique may help with the longevity of the system 10 because as any LEDs of illumination source 38 begin to wear, the exposure technique can make adjustments in exposure time, thereby allowing illumination source 38 to last longer. Imaging unit 32 may be interfaced with the electronic control board 36 of reader 12 for communication with reader 12, including display 14 and control panel 16.

Figure 4:
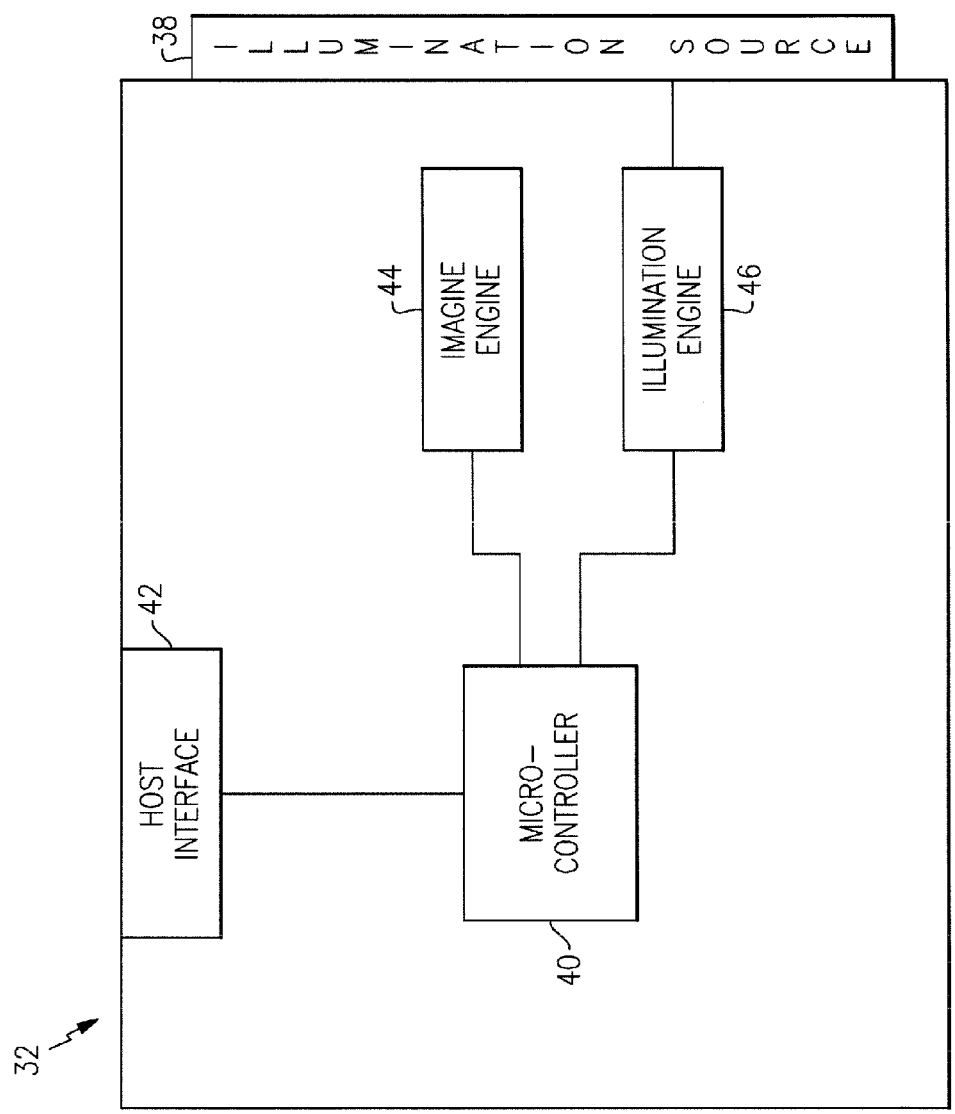
FIG. 4 is a schematic of an imaging unit according to the present invention.

Referring to FIG. 4, imaging unit 32 preferably includes an on-board illumination source 38 comprising one or more light emitting diodes (LEDs) of selected wavelengths, to provide illumination of strip 22 when cartridge 20 is inserted into reader 12. LED wavelength is selected to provide the best sensitivity to color changes in the indicating compound. Alternatively, illumination source 38 may be separately attached to imaging unit 32 and positioned proximately thereto, provided that uniform illumination of strip 22 area is maintained. Imaging unit 32 further includes a microcontroller 40 for managing imaging and illumination operations, performing processing of captured images, and communicating with a remote device, such as a host computer or on-board system microcontroller, if desired. For example, imaging unit 32 may include a host interface 42, such as a conventional RS232 transceiver and associated 12-pin jack. Alternatively, interface 42 may comprise other conventional bus protocols, such as USB, IEEE, 1394, IrDA, PCMCIA, or Ethernet (TCP/IP). Interface 42 may also comprise a wireless transceiver for wireless communication to a host computer and is programmed with the applicable protocols for interfacing with a host computer, such as Bluetooth(r) or 802.11 protocols.

Microcontroller 40 is interconnected to an imaging engine 44 to control the optical imaging of a target object, such as strip 22, and forming corresponding electrical image data. Microcontroller 40 is also interconnected to an illumination engine 46 for controlling the timing and illumination level of illumination source 38 during imaging operations. Optionally, imaging engine 44 and illumination engine 46 may be provided as a single unit interconnected to microcontroller 40. For example, imaging unit 32 may comprise an IT4X10/80 SR/SF or IT5X10/80 series imager available from Hand Held Products, Inc. of Skaneateles Falls, N.Y. The IT5X10/80 series imager is a CMOS-based decoded output engine that has image capture capabilities via an 8-bit A/D converter. Imaging unit 32 obtains an optical image of the field of view and uses preprogrammed algorithms to analyze the contents of the image. Microcontroller 40 may comprise a MC9328MXL VH15 microprocessor, available from Freescale Semiconductor, Inc. of Chandler, Ariz., that is programmed prior to implementation in imaging unit 32, or programmed anytime thereafter, such as by using interface 42 to upgrade the firmware used for microcontroller 40. Alternatively, firmware upgrades may be performed using a removable ROM device that contains executable software that is downloaded to both microcontroller 40 and imaging unit 32 at runtime.

As will be explained hereinafter, imaging unit 32 (e.g., microcontroller 40) may be programmed to with image processing algorithms, such as shape recognition, culling, matched filtering, statistical analysis, and/or other high-level processing techniques, to interpret the optical properties of control region 28, sample region 30, and background portions 48 after the placement of a liquid sample on strip 22. Microcontroller 40 is thus programmed to perform all of the image interpretation functions for system 10. Because microcontroller 40 is connected to the optics of imaging unit 32 via high speed data transfer links, such as a standard video port found on such microcontrollers, image analysis is significantly faster than in conventional systems where image data must be transferred from the imaging unit and local imaging microcontroller to a more remote host microcontroller for processing. While system 10 further includes a host microcontroller 50 interconnected to display screen 14 and control pad 16 for user interaction and control of the general operations of system 10, microcontroller 40 of imaging unit 32 is dedicated to image processing. As a result, only a limited amount of data needs to be transferred from imaging unit 32 to host microcontroller 50, i.e., only the results of the image analysis rather than the large image files associated with the capture of images of cartridge 20 need to be transferred to host microcontroller 50 for control and display operations.

The presence and concentration of the target compound may be determined in system 10 by comparing the degree of reaction of sample region 30 relative to control region 28 based on the relative contrast between sample region 30 and control region 28. The present invention thus determines the concentration of a target compound in a sample, such as an antibiotic drug in milk, by measuring the ratio of mean reflected intensity of control region 28 to the mean reflected intensity of sample region 30, relative to the mean reflected intensity of the substrate, i.e., background portions 48.

For example, in FIG. 5A, sample region 30 is significantly less intense than control region 28, thereby indicating that there are no detectable amounts of the target compound. In FIG. 5B, sample region 30 is only marginally less intense than control region 28, thereby indicating low levels of the target compound. In FIG. 5C, sample region 30 is the same intensity as control region 28, thereby indicating greater amounts of the target compound, such as the threshold concentration requiring reporting to a governmental authority. In FIG. 5D, sample region 30 is significantly more intense than control region 28, thereby indicating unacceptably high concentrations of the target compound. It should be recognized that the relative intensity of sample region 30 may be used to determine the precise concentration of a target compound in a liquid sample because predetermined degrees of relative intensity may correspond to particular concentration levels of a target compound.

Figure 6:
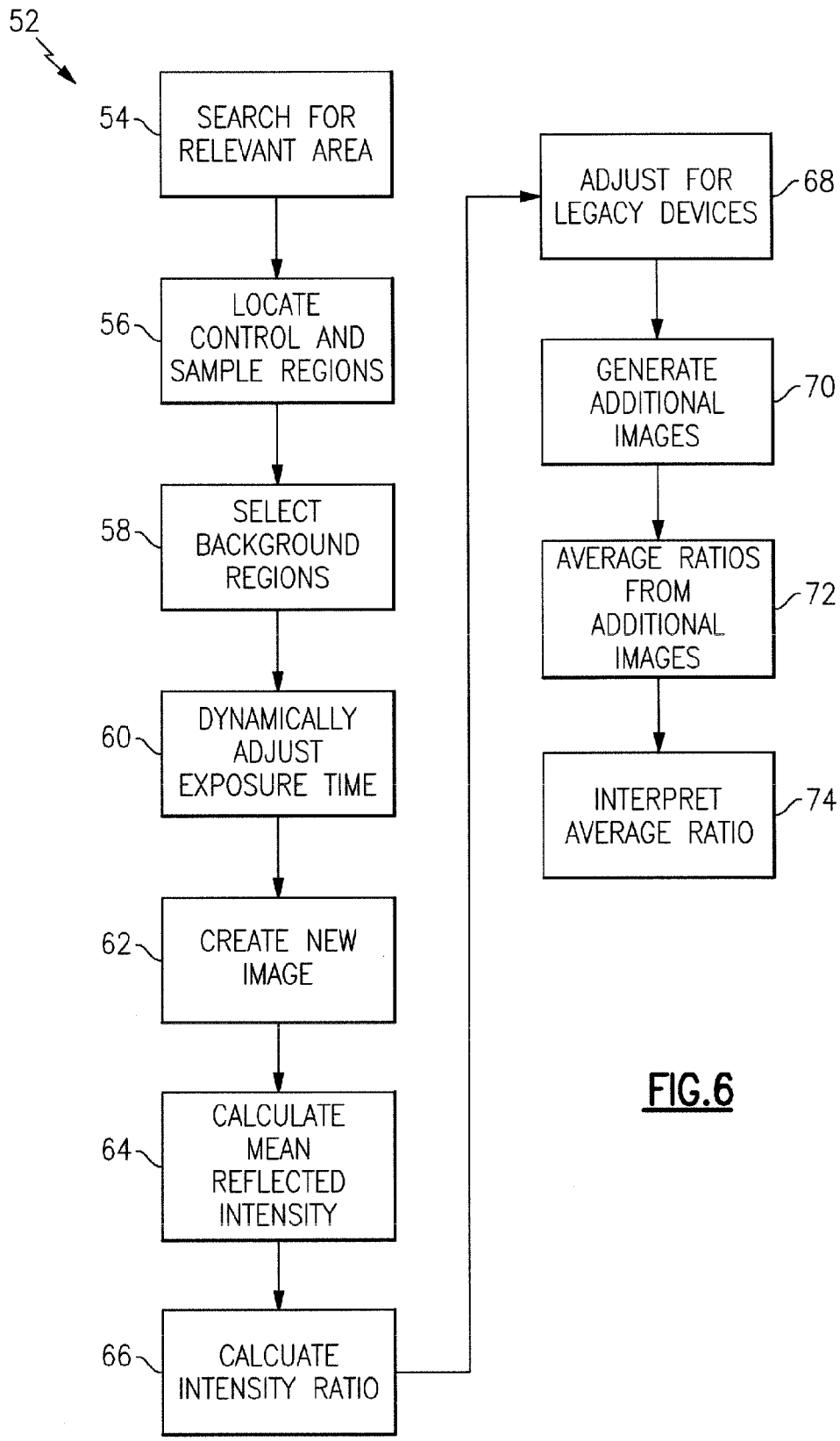
FIG. 6 is a high-level flowchart of an image interpretation process according to the present invention.

Microcontroller 40 implements an image interpretation process 52, as seen in FIG. 6. From a high-level standpoint, process 52 comprises the following steps. First, a search is performed 54 inside a captured image to locate the relevant area of strip 22 that contains control region 28 and sample region 30. Exposure time of the imaging sensor may be adjusted to optimize the location accuracy in this step. Next, control region 28 and sample region 30 are located 56 in the image. Suitable background regions 48 outside of control region 28 and sample region 30 are then chosen 58 to represent the reflectance of the substrate of strip 22. The exposure time is then adjusted recursively 60 until a predetermined minimum mean reflected intensity in the background areas is obtained. A new image is then created 62 using this exposure. The mean reflected intensities of the control region 28, sample region 30, and background regions 48 are then calculated 64. The intensity ratio of control region 28 to sample region 30, adjusted for the reflectance of strip 22, is then calculated 66. The resulting ratio may optionally be adjusted 68 to approximate a numerical match to the output of legacy devices if appropriate. Next, additional images are generated in sequence 70 using the same optimal exposure and spot location data as described above, and the same mean reflected intensity and ratio calculations are performed 72 for each image and averaged ratio over the images. Preferably, nine additional images are generated. Finally, the resulting average ratio is interpreted 74 to detect and quantify the presence or absence of the target compound.

It should be recognized by those of skill in the art that the location of control region 28, sample region 30, and background regions 48 may be accomplished using various image processing algorithms, ranging from mathematical morphology to template matching. Preferably, reader 10 implements a spot location algorithm 80 that optimizes the location accuracy, calculation speed, and computation complexity.

Figure 7:
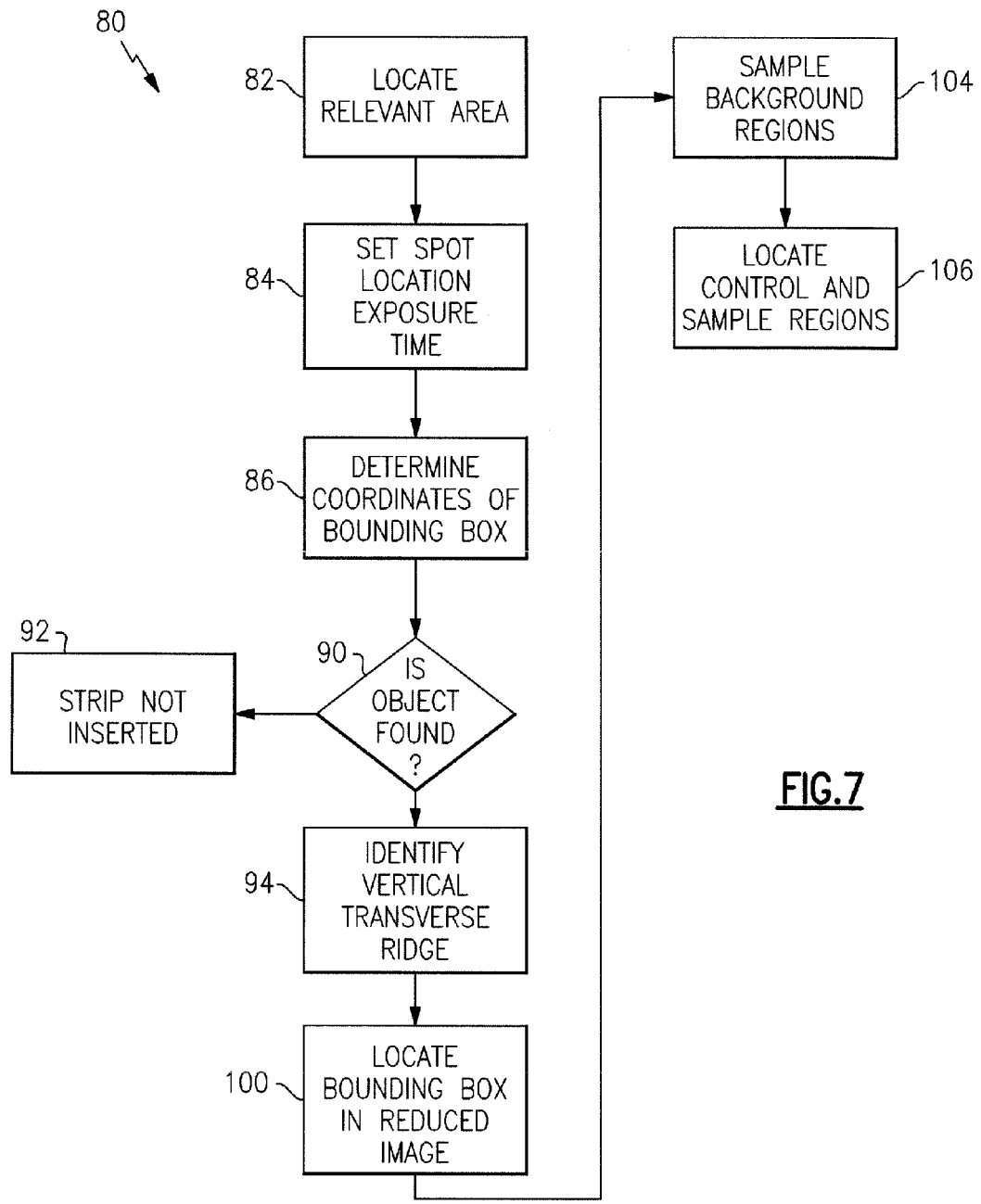
FIG. 7 is a flowchart of a spot location process according to the present invention.
Figure 9:
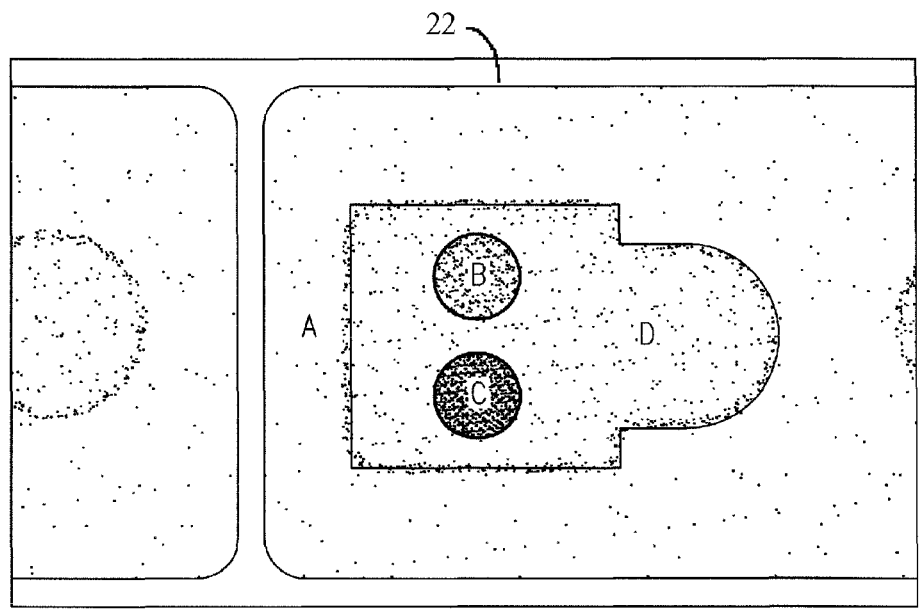
FIG. 9 is an image of a strip according to the present invention.
Figure 10:
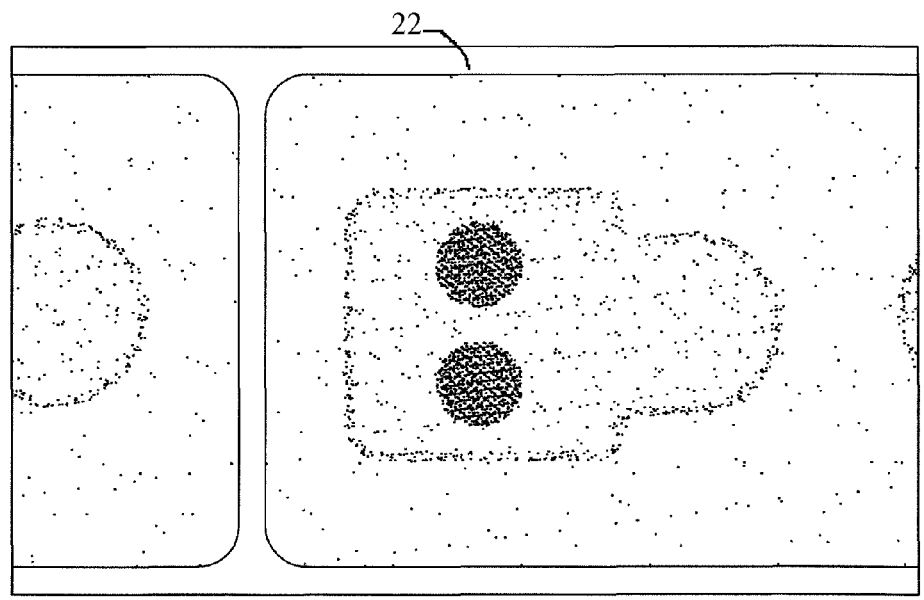
FIG. 10 is an adjusted image of a strip according to the present invention.
Figure 11:
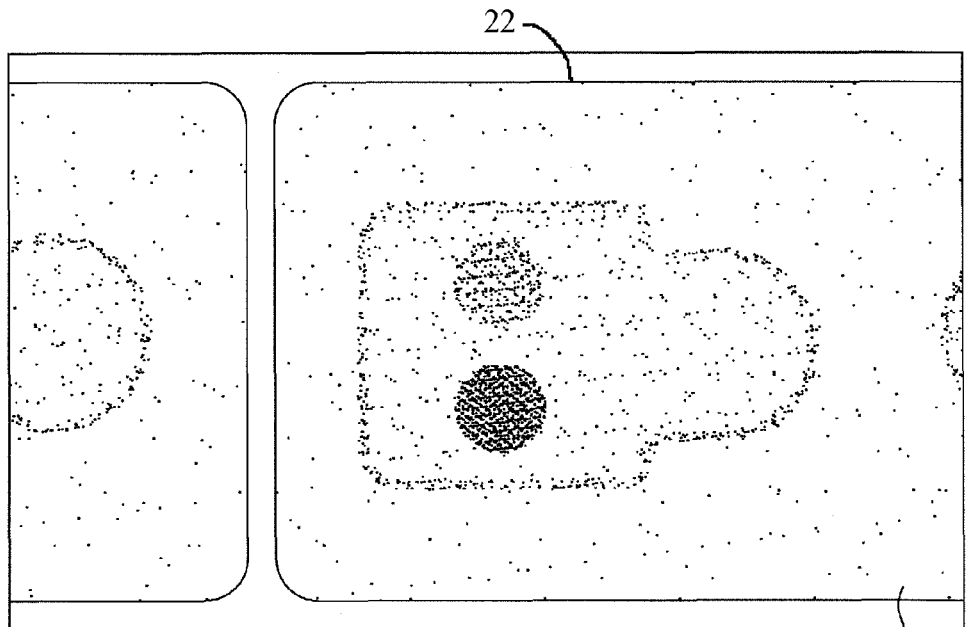
FIG. 11 is an image of a strip according to the present invention.

As seen in FIG. 7, the first step in location algorithm 80 is to locate the relevant area of strip 22 within the captured image 82. Referring to FIG. 9, an image of a two-spot strip 22 is shown as an example taken with the appropriate exposure. The imaging exposure time is dynamically determined 84 such that the surface of the inserted strip 22 consists of the largest, closed white object in comparison with the deep dark background in the captured image. As shown in FIG. 10, hard limiting may be used to segment the image into objects of interest within the background. Using the limited image, either an image segmentation technique or a lateral histogram technique can be used to determine the coordinates 86 of a bounding box that tightly encloses the surface of strip 22, as illustrated in FIG. 11. The region of interest may then be extracted for the later processing. If a check 90 determines that no object may be found in the middle of the image, or if the found object is too small (or the area of the surrounding box is too small), a decision may be made 92 that strip 22 has not been inserted correctly.

Figure 12:
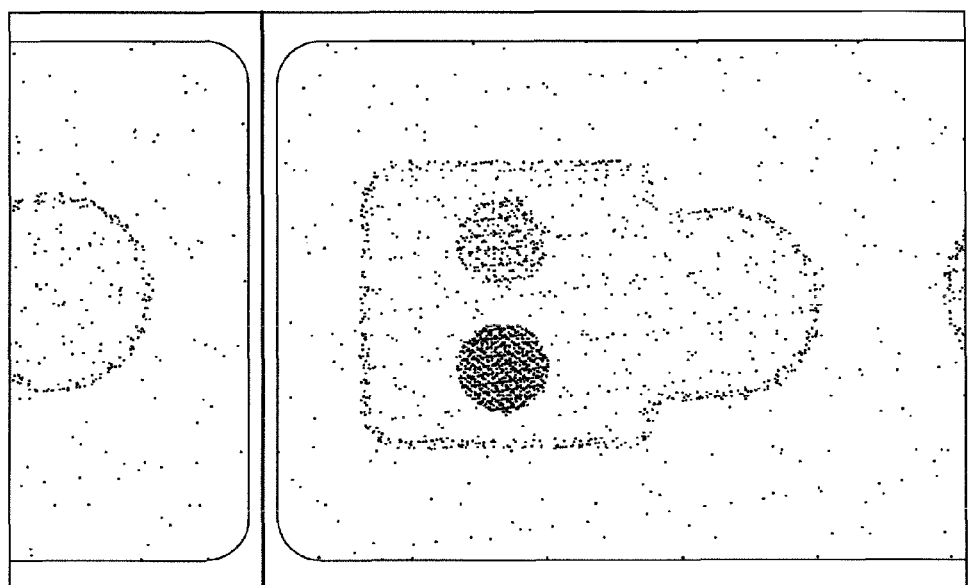
FIG. 12 is an image of a strip showing a transverse ridge according to the present invention.
Figure 13:
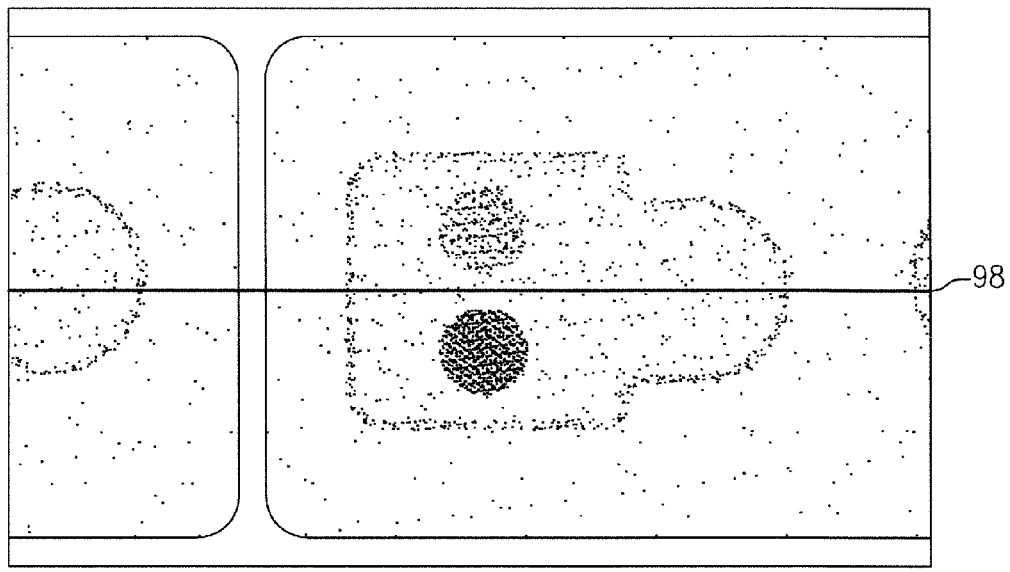
FIG. 13 is an image of a strip showing a center line according to the present invention.
Figure 15:
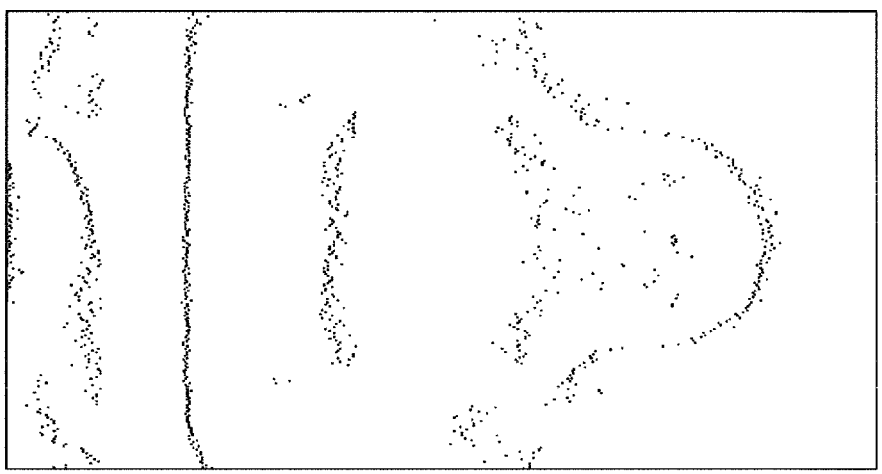
FIG. 15 is an enhanced sub-image of a strip according to the present invention.
Figure 14:
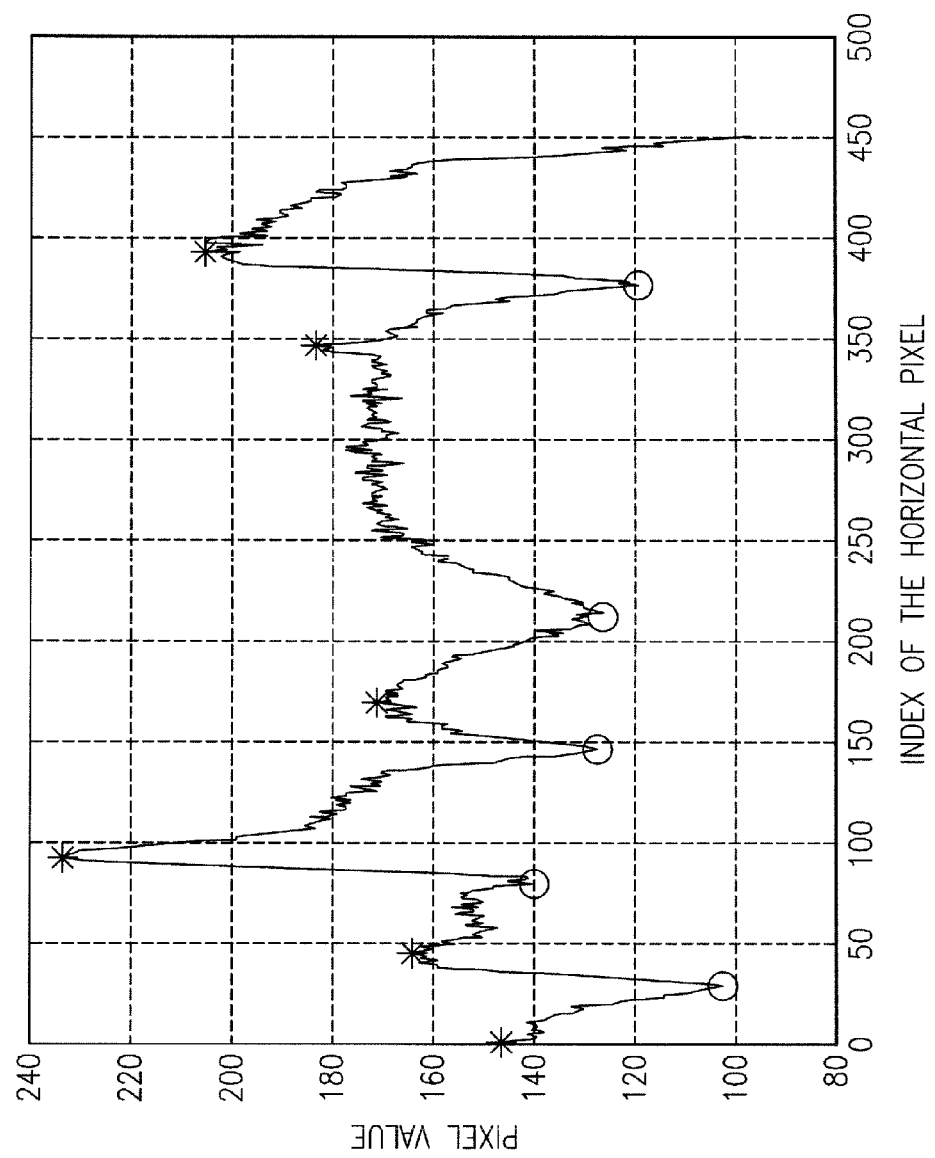
FIG. 14 is a chart illustrating the pixel magnitude profile along the center line according to the present invention.

The next step in location algorithm 80 is the identification 94 of a transverse ridge 94, which is a strong line of dark pixels to bright pixels located at the left of the center of the extracted image region, as highlighted in FIG. 10. Transverse ridge 94 is salient because it is the longest vertical edge transiting from left dark image region to bright right image region. Common edge detection algorithms can be used to detect this ridge by locating the longest vertical edge. However, in order to minimize computation, an efficient method for performing this transverse vertical line detection is to trace and detect the significant peaks of image pixels along each row of the image region. According to this method, transverse ridge 96 is located by considering the pixel values along a horizontal line 98, as seen in FIG. 13. FIG. 14 illustrates the pixel magnitude profile of horizontal line 98, with the detected significant peaks and valleys denoted to illustrate the locations of the detected peaks of the pixel values on every row of the image (which are white pixels). These detected peaks correspond to the vertical edges of vertical ridge 96 of FIG. 12. FIG. 15 depicts the location of the transverse ridge after visualizing the column accumulating the largest number of horizontal peaks.

Locating transverse ridge 96 and checking its location helps to determine whether strip 22 is in the proper orientation. If transverse ridge 96 is detected to be located to the right of center, strip 22 may have been inserted backwards or incompletely. In such cases, reader 10 can report an error. Because transverse ridge 96 separates the substrate area from the product insertion area, once detected, it is possible to refine the region of interest further and speed up the subsequent processing by using only the region to the right of transverse ridge 96.

Figure 16:
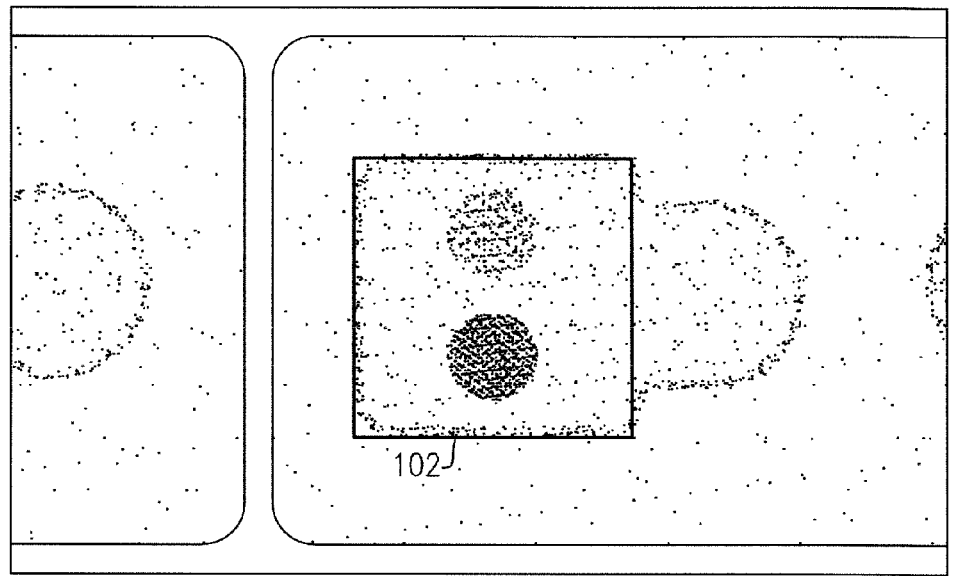
FIG. 16 is an image of a strip including a bounding box according to the present invention
Figure 17:
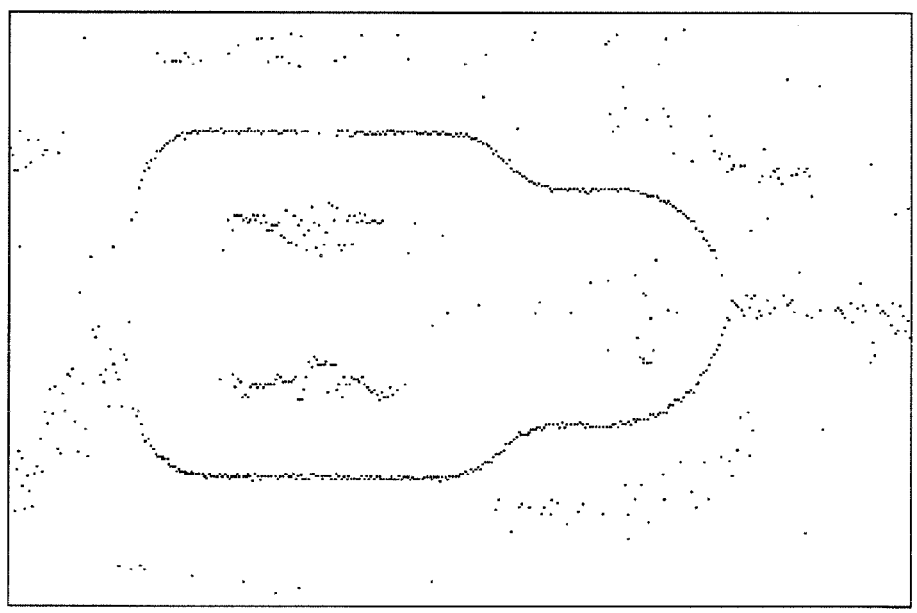
FIG. 17 is an enhanced sub-image of a strip according to the present invention.
Figure 18:
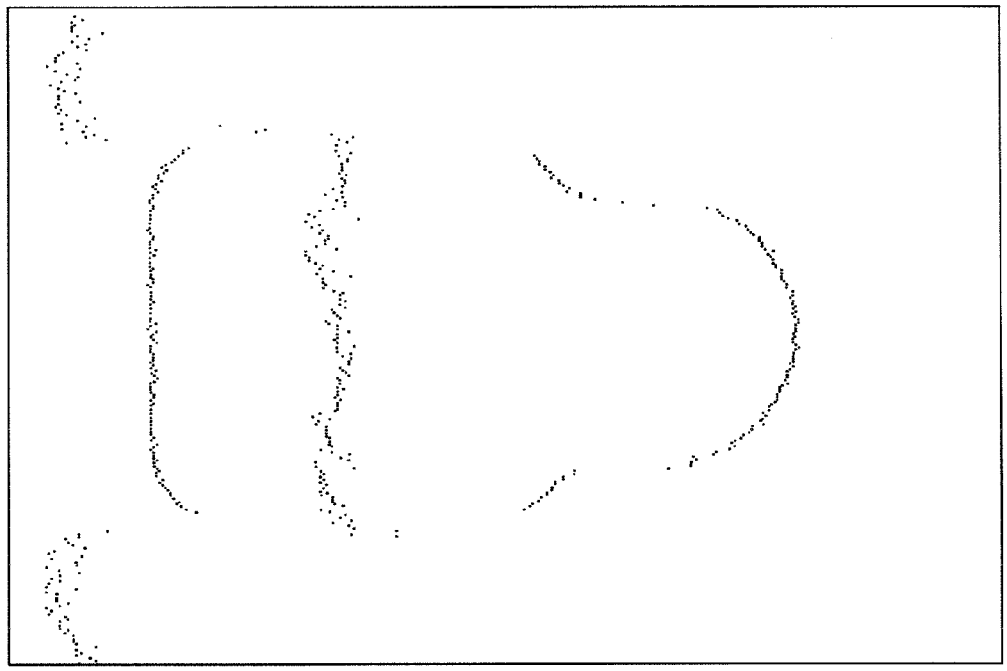
FIG. 18 is another enhanced sub-image of a strip according to the present invention.

After the transverse ridge is detected, the next step is to further analyze the defined region of interest, seen in FIG. 16, to locate 100 a bounding box 102 that encompasses control region 28, sample region 30, and background regions 48. Since the substrate region is in a lower intensity basin relative to its surrounding bright background, the pixels on the boundary of the substrate coincide with the valley pixels of each column and row of the sub-image. The same technique used for locating vertical ridge 96 may then be applied, but instead of tracing the peaks, the boundary of the relevant substrate region is detected by tracing the valleys of each row and column of the sub-image, as seen in FIGS. 17 and 18. The top and bottom lines of box 102 are detected by finding the uppermost and lowermost rows that have the significant valleys in FIG. 17. The left line is detected by finding the rightmost column that has the significant horizontal valleys in 18, while the right line is detected by tracing the ends of the detected top and bottom line in FIG. 17. The pixel coordinates of the located reference substrate bounding box are used as the reference coordinates for subsequent steps of the spot location procedure.

Figure 19:
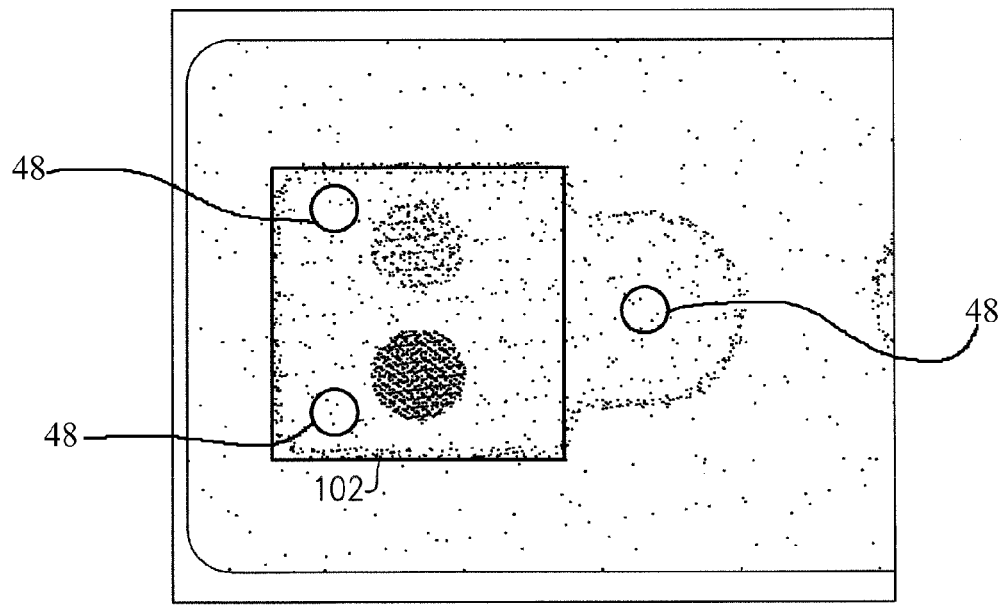
FIG. 19 is an image of a strip illustrating background regions according to the present invention.

The next step is to correctly compute the ratio of control spot to sample spot color intensity (C/S), which requires sampling 104 of the pixel values of background regions 48. As an example, three background regions 48 that are geographically separated on the substrate may be selected, as seen in FIG. 19. The locations of these three background regions 48 should be chosen to best represent the substrate background reflectance and be least likely to be contaminated by control region 28 and sample region 30.

Figure 20:
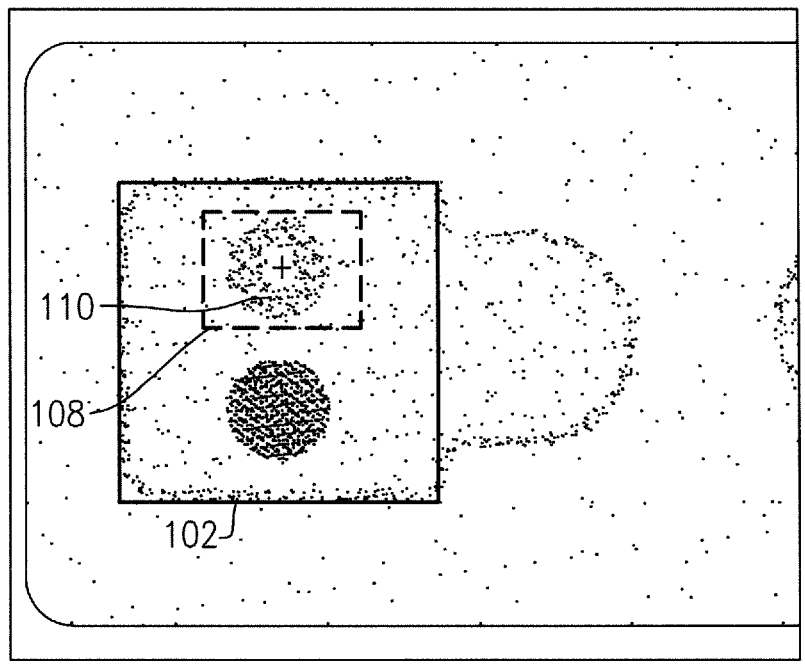
FIG. 20 is an image of a strip illustrating a control region search window according to the present invention.
Figure 21:
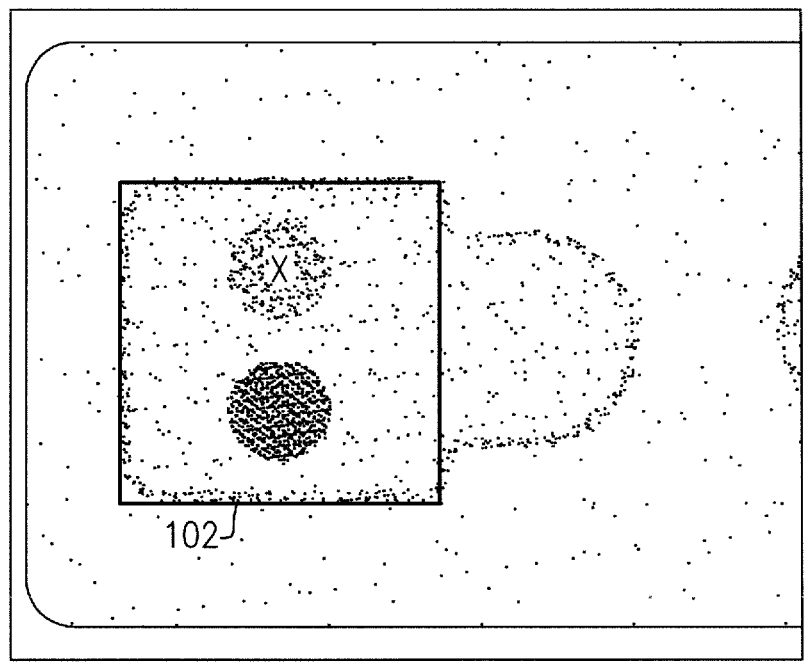
FIG. 21 is an image of a strip illustrating selection of the pixels in control region according to the present invention.
Figure 22:
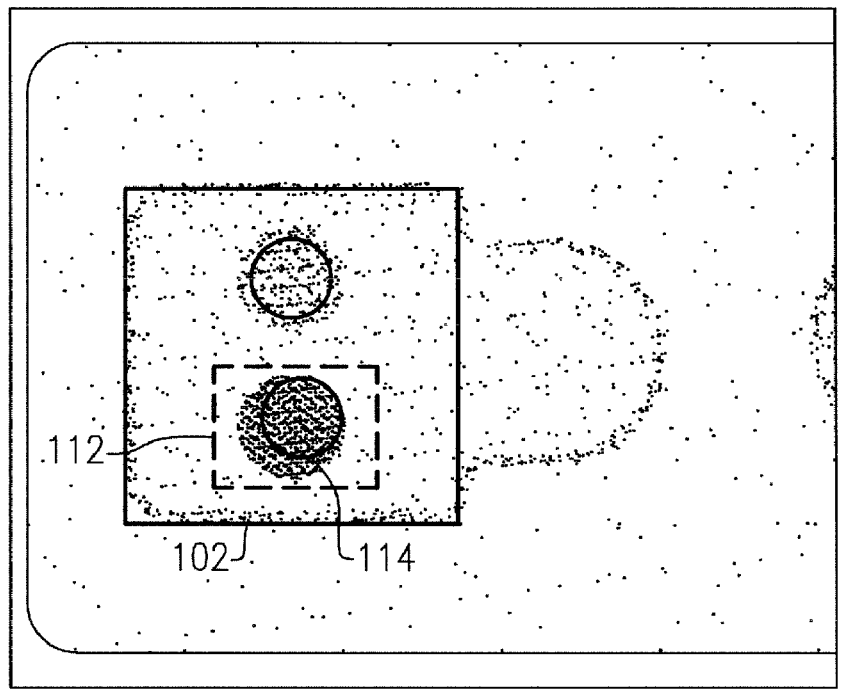
FIG. 22 is an image of a strip illustrating a sample region search window according to the present invention.
Figure 23:
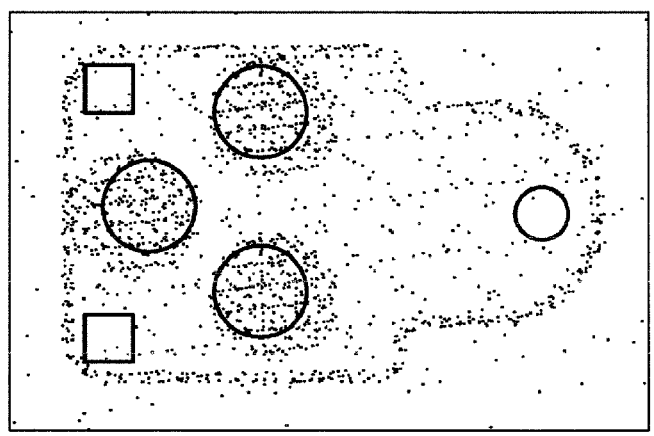
FIGS. 23 through 26 are images of different embodiments of strips showing regions of interest according to the present invention.
Figure 24:
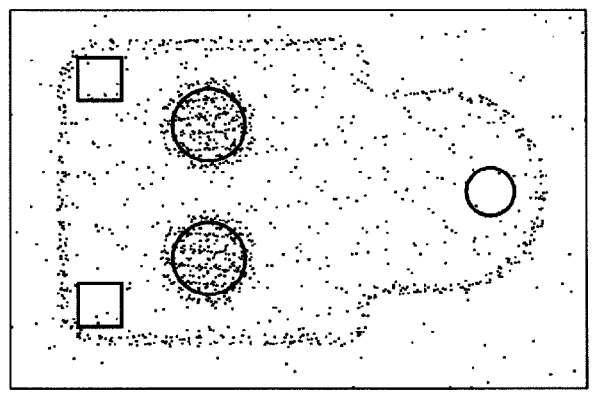
Figure 25:
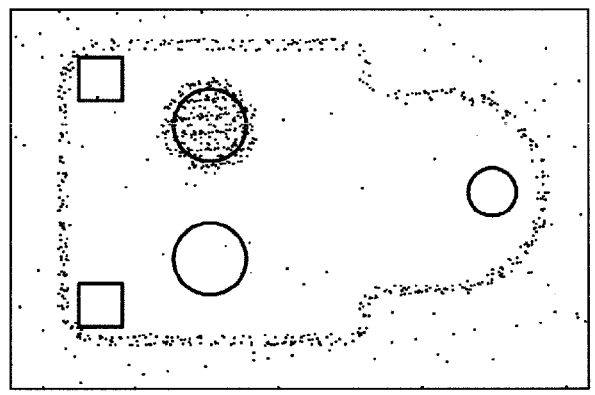
Figure 26:
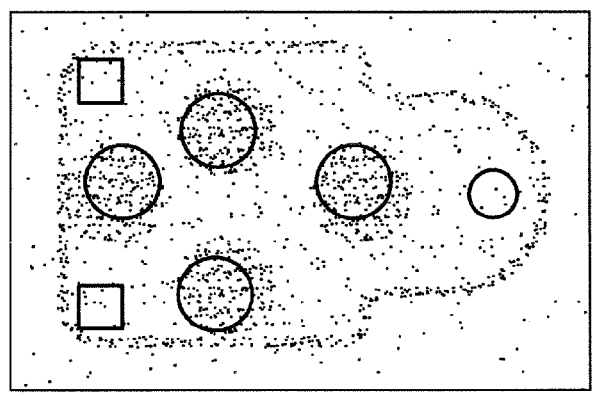

The final step 106 is to locate control region 28 and sample region 30. As seen in FIG. 20, control region 28 is located first before sample region 30. The search window for control region 28 is first defined according to the reference substrate bounding box 102 of FIG. 16. The center of control region 28 is initially determined by looking for the lowest valleys point of the bilateral histograms of the pixels in the control spot search window 108, as seen in FIG. 20. In FIG. 20, control region center 110 corresponds to the lowest valley of the vertical and horizontal histogram. Located control region 28 is refined by maximizing the contrast of all the pixels inside control region 28 with respect to the background regions 48, as seen in FIG. 21. After control region 28 has been found, sample search window 108 and sample center 110 are used to determine a sample search window 112 for sample region 30, as seen in FIG. 22. The sample center 114 is then determined in the same manner as control center 110 of control region 28. For applications with more sample regions 30, multiple sample regions 30 may be searched in the middle left and middle right of the reference substrate rectangle according to the device specifications, as seen in FIGS. 23 and 26.

To obtain the best possible accuracy for measurement of ratio, a different exposure should be determined to maintain the highest possible mean reflected intensity of background regions 48 without A/D converter saturation. Establishing the optimal exposure levels may be accomplished by determining the mean reflected intensity of background regions 48 after control region 28 and sample region 30 have been located. If the background MRI is different from the desired nominal value, the correct exposure is determined iteratively, and subsequent exposures are made using the optimal exposure setting. The mean reflected intensities of control region 28, sample region 30, and background regions 48 are then calculated using the sample areas determined from the first image.

Figure 8:
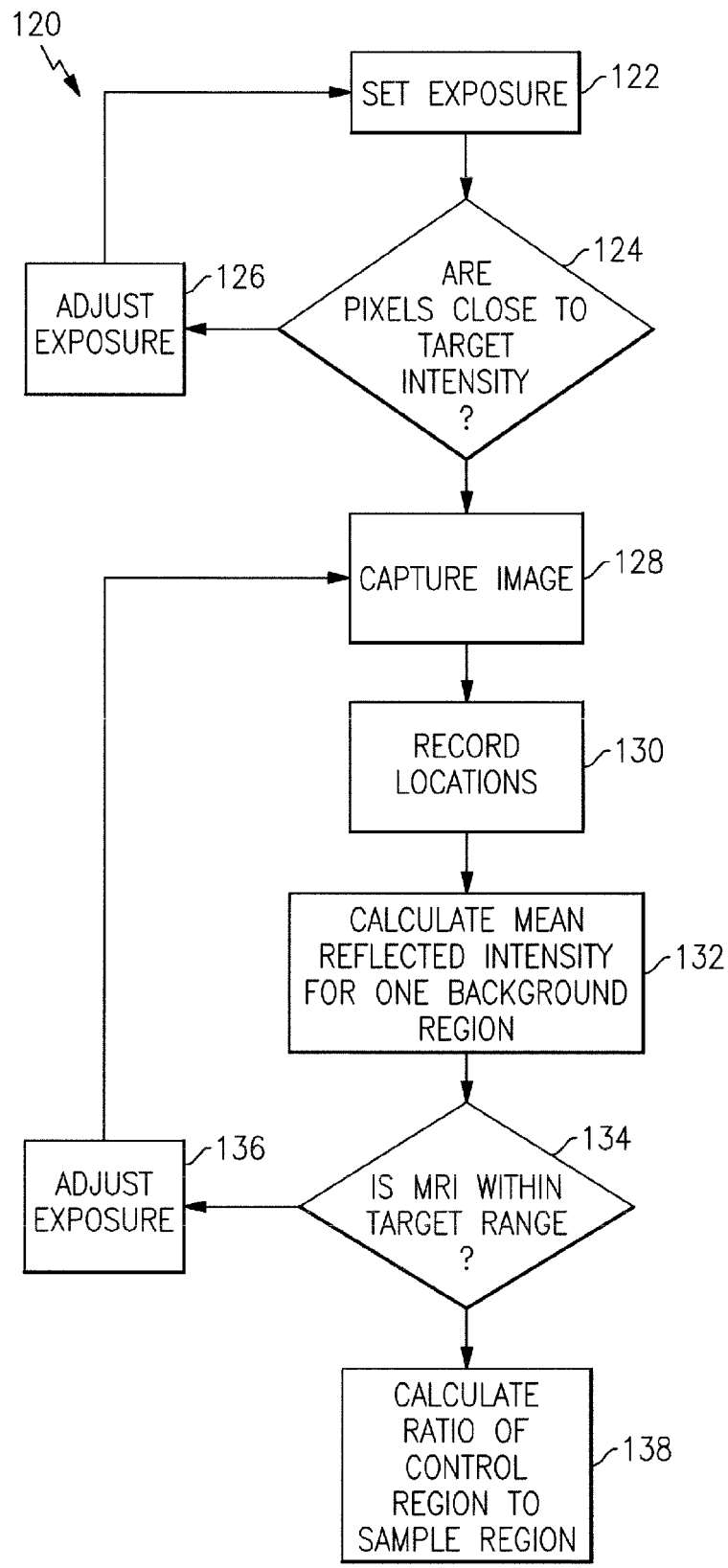
FIG. 8 is a low-level flowchart of an image interpretation process according to the present invention.

More particularly, as seen in FIG. 8, the first step in the exposure optimization process 120 involves setting up the initial exposure 122 to enable detection of control region 28, sample region 30, and background regions 48. Images that are too dark or too bright inhibit correct detection. Using a default exposure to get first images for detection, the middle area of the images may be checked 124 to see if the pixels are close to the target image intensity. If not, the exposure time may be increased or deceased 126, and the procedure repeated until the suitable exposure for location is determined.

The next step is to capture the image 128 at the final exposure obtained in the first step and then control region 28, sample region 30, and background regions 48. The locations are recorded 130 for use in the next step. The mean reflected intensity is then calculated 132 for one background region 48 seen in FIG. 18, and a check is performed 134 to determine whether the image has the optimal exposure. If the mean reflected intensity of background region 48 is outside of the targeted range, the exposure time is increased or decreased 136, and images are taken again until the background mean reflected intensity reaches target value. If the mean reflected intensity of background region 48 is within the targeted range, the exposure determined in the second step is used to obtain ten sequences of images. For each such image, the mean reflected intensities of control region 28, sample region 30, and background regions 48 are used to calculate the ratios, which are averaged 138 to determine the final result.

The mean reflected intensity of an area is computed as the average value of pixels inside a circle centered on the located spot center. Examples of such areas are shown in FIGS. 23 through 26 for different strips 22. The objective is to compute the mean reflected intensity as the value most representative of the color intensity of the spot. However, due to potential inaccuracies in spot location, fuzzy spot boundaries, or imaging sensor noise, some of the pixels contained within a selected area should not be included in the average. The degrading effect of such pixels is mitigated by discarding the ten percent brightest pixels and the ten percent darkest pixels inside the spot area, and then computing the mean reflected intensity using only the central eighty percent of the histogram. This procedure works both for control region 28, sample region 30, and background regions 48. As seen in FIGS. 22 through 25, three background regions 48 may be used to determine an average background mean reflected intensity, i.e., two square areas on the left side of the image and one small round area on the right side of the image. The mean reflected intensity of each background spot is computed and the average value of the three results is used as the background mean reflected intensity for calculation of the ratio (C/S).

The C/S ratio is calculated using the following procedure:

$$C/S = \frac{M_B - M_C}{M_B - M_S}$$

where $M_B$ is the background MRI, $M_C$ is the control spot MRI, and $M_S$ is the sample spot MRI. In some cases, the C/S ratio may need to be adjusted to provide a numerical match with values that are produced by previous generations of readers 10. This is required to avoid confusing users of the product when they replace old equipment with new.

The final ratio, R, may be calculated using the following piecewise linear function:

IF $C/S$<1.576 THEN Ratio=1.1212*$C/S$−0.0815
ELSE Ratio=0.5961*$C/S$+0.746

This function was determined empirically by analysis of two-spot samples containing various concentrations of Amoxicillin from 0 to 10 ppb. The resulting value of R is used both for display and for purposes of interpretation. The interpretation output is generated by comparing the ratio, R, with a threshold value, $T_D$, which is (currently) independent of the type of drug being tested. For values of $R>T_D$ the interpretation output is a 1. Otherwise it is a 0. A typical value of $T_D$ is 1.02. The threshold may vary for different drugs and this function may be different for different applications. A quadratic function, an exponential function, or a logarithmic function may be found, for example, to fit the data better than a piecewise linear function. Coefficients of the selected function may be changed based on more extensive comparative testing.

The final ratio may then be used to determine the concentration of the substance using predetermined lookup tables or simple displayed for a user. Table 1 below depicts example R values and the corresponding concentration of amoxicillin:

TABLE 1

| R Value | Concentration of Amoxicillin |
|---------|------------------------------|
| 0.80    | No detectable amount         |
| 1.06    | 4 ppb                        |
| 1.30    | 10 ppb                       |

The R values and respective concentration levels may be calibrated by using sample liquids having known concentration levels and calculating the R values in system 10. Once a baseline correlation is established, the R values and corresponding concentrations may be stored in memory and retrieved for display to a user after the R value for an unknown sample concentration is calculated. It should be recognized by those of skill in the art that the R values and corresponding concentrations will vary depending on the physical configuration of system 10, e.g., the lighting level, focal distance, exposure setting, gain, etc., and will also vary between target compounds, e.g., penicillin verses amoxicillin. Accordingly, dissimilarly configured systems 10 will need to be configured independently.

Figure 27:
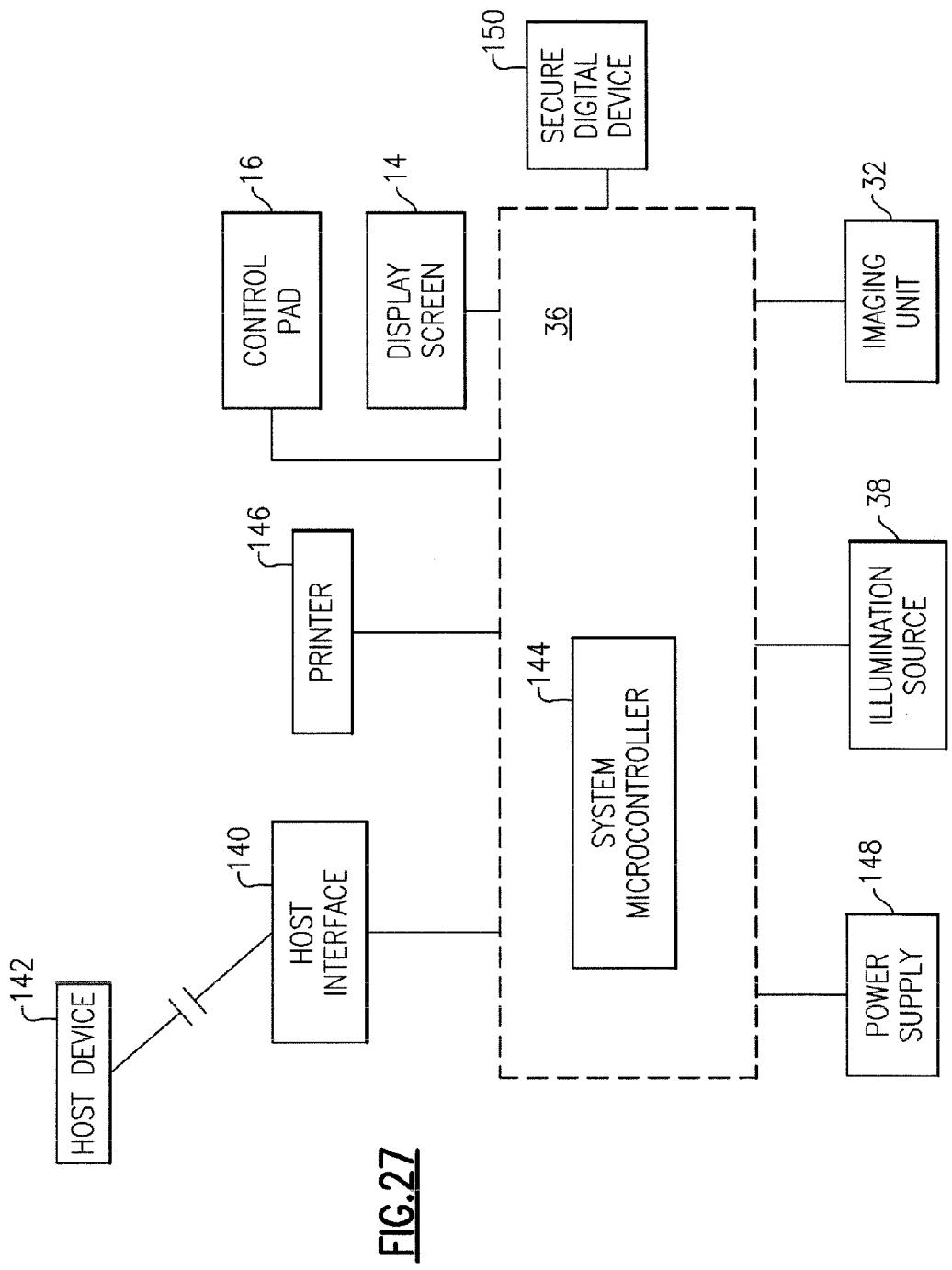
FIG. 27 is a schematic of a clinical sampling system for interconnection to a host device according to the present invention.

As seen in FIG. 27, electronic control board 36 of reader 12 may include an external interface 140 for interconnection to a host device 142, such a computer. Interface 140 may comprise any standard computer interface, such as a USB port. Electronic control board 36 preferably includes a system microcontroller 144 interconnected to interface 140 and the other elements of system 10, such as display screen 14 (or touch screen), control pad 16 (or user keyboard), imaging unit 32, an internal or external printer 146, a power supply 148, a separate illumination source 38, as desired. In this manner, system microcontroller 144 may be programmed to respond to conventional or custom host PC commands, thereby acting as a slave device and allowing a user to externally control system 10 using an attached computer as host device 142. A user may then upload test results to create an electronic record, or print paper records from a printer attached to host device 142. Using host device 142 or control pad 16, a user may alternatively direct that test results be printed on printer 146 attached to system 10.

The ability of system 10 allow for the attachment of host device 142 and interaction therewith allows a user to more easily upgrade or make changes to software running on microcontroller 40 of imaging unit 32 or the software running on system microcontroller 144. Preferably, system 10 includes a secure digital device 150 interconnected to electronic control board 36 for upgrades performed in the field.

The use of microcontroller 40 and system microcontroller 144 also allows an attached host device 142 to emulate system 10. Using emulation software, an attached computer may mimic the user graphical interface of system 10 and perform the operations of electronic control board 36 remotely, thereby allowing a user of host device 142 to control system 10 from an the attached computer. In this manner, and through the use of host commands sent to and executed by system microcontroller 144, host device 142 may effectively substitute as system microcontroller 144 and direct substantially all of the operations performed independently by system microcontroller 144. For example, host device 142 may reproduce data presented on display screen 14 and allow for user entry of information, thereby bypassing display screen 14 and control pad 16 and allowing a user to control system 10 via host device 142 as if using system 10 directly.

Similarly, host device 142 may be enable to communicate with microcontroller 40 of imaging unit 32, such as by sending commands, such as an image capture command, or receiving data, such as image data captured by imaging engine 44. Thus, host device may be provided with software for performing any of the imaging processing algorithms discussed herein, software for performing alternative or improved image processing algorithms, or software for implementing testing algorithms to assist in more effectively processing image data, software for diagnosing problems with image processing techniques, or software for calibrating image processing functions. Host device 142 may also be used to record and archive captured data, or electronically transmit captured or interpreted data to a remote location for further analysis. For example, due to the limited availability of space, non-volatile memory resident in system 10 may be restricted and host device 142 may be used for expanded memory capabilities.

What is claimed is:

1. An apparatus for determining the presence of at least one target compound in a sample, comprising:
   a housing having a slot formed therein;
   a cartridge including a reaction strip having a sample region, a control region, and a background region located therein that is adapted for insertion into said slot;
   an optical imaging unit including an optical imager interconnected to a microcontroller positioned with said housing to capture images of said cartridge when inserted into said slot, and wherein said microcontroller is programmed to process said image to identify the location of said sample region, said control region, and said background region after said cartridge is inserted into said slot.

2. The apparatus of claim 1, wherein said microcontroller is programmed to calculate a value representing the ratio of the mean reflected intensity of said sample region relative to the mean reflected intensity of said control region, relative to the mean reflected intensity of the background region.

3. The apparatus of claim 2, wherein said microcontroller is programmed to detect the presence of said at least one target compound based on said ratio.

4. An apparatus for determining the presence of at least one target compound in a sample, comprising:
   a housing having a slot formed therein;
   a user interface mounted in said housing;
   a host microprocessor positioned within said housing and interconnected to said user interface;
   a cartridge including a reaction strip having a sample region, a control region, and a background region located therein that is adapted for insertion into said slot; and
   an optical imaging unit including an optical imager interconnected to a microcontroller positioned within said housing for capturing images of said cartridge when inserted into said slot, and wherein said microcontroller is programmed to process said image to identify the location of said sample region, said control region, and said background region after said cartridge is inserted into said slot.

5. The apparatus of claim 4, wherein said microcontroller is programmed to calculate a value representing the relative intensity of said sample region relative to said control region.

6. The apparatus of claim 5, wherein said microcontroller is programmed to determine the presence of said at least one target compound based on said value representing the relative intensity of said sample region relative to said control region.

7. A process for determining the presence of a target compound in a liquid, comprising the steps of:
   placing a portion of said liquid on a test strip;
   inserting said test strip in a reader;

capturing an optical image of said test strip after insertion in said reader;

identifying the location of a test region, a control region, and a background region on said test strip by digitially analyzing said optical image; and interpreting said image to determine the presence of said target compound based on said test region, said control region, and said background region.

8. The process of claim 7, further comprising the step of determining the concentration of said target compound in said liquid.

9. The process of claim 7, wherein said control region is treated to serve as a control, and said sample region is treated to serve as an indicator of the presence of said compound.

10. The process of claim 9, wherein the step of interpreting said image to determine the presence of said target compound comprises the steps of:

identifying the mean reflected intensity of said control region;

identifying the mean reflected intensity of said sample region;

determining the ratio of the mean reflected intensity of said control region to said sample region.

11. The process of claim 10, further comprising the step of identifying the mean reflected intensity of at least one background region.

12. The process of claim 11, wherein the step of determining the ratio of the mean reflected intensity of said control region to said sample region is determined relative to the mean reflected intensity of said at least one background region.

* * * * *